United States Patent [19]

Ohwaki et al.

[11] Patent Number: 5,468,623

[45] Date of Patent: Nov. 21, 1995

[54] METHOD OF CONVERTING BIG ENDOTHELIN-1 TO ENDOTHELIN-1 WITH HUMAN APOLIPOPROTEIN B

[75] Inventors: Tatsuya Ohwaki; Hiroshi Sakai, both of Ohimachi, Japan

[73] Assignee: Nisshin Flour Milling Co., Ltd., Tokyo, Japan

[21] Appl. No.: 393,036

[22] Filed: Feb. 23, 1995

Related U.S. Application Data

[63] Continuation of Ser. No. 308,543, Sep. 21, 1994, abandoned.

[30] Foreign Application Priority Data

Sep. 21, 1993 [JP] Japan ..................... 5-234650

[51] Int. Cl.$^6$ .............. C12P 21/02; C12N 9/48; C12N 9/50; C12N 9/64
[52] U.S. Cl. .............. 435/68.1; 435/212; 435/219; 435/226
[58] Field of Search .............. 435/68.1, 212, 435/219, 226

[56] References Cited

FOREIGN PATENT DOCUMENTS

| 0257778 | 3/1988 | European Pat. Off. . |
| 0347915 | 12/1989 | European Pat. Off. . |
| WO92/06994 | 4/1992 | WIPO . |
| 92013944 | 8/1992 | WIPO . |

OTHER PUBLICATIONS

Ohwaki et al. (1993) *Atherosclerosis,* 102(2), 227–228.
Ohnaka et al. (1993) *J. Biol. Chem.,* 268(35), 26759–26766.
Ikura et al, (1994) *Biochem. Biophys. Res. Comm., 203(3),* 1417–1422.
Okada et al. (1990) *Biochem Biophys. Res Comm.,* 171(3), 1192–1198.
Sawamura et al, (1990) *Biochem. Biophys. Res Comm.,* 172(2), 883–889.
Sawamura et al, (1993) *Biohim. Biophys. Acta,* 1161, 295–302.
Sakai et al. (19 Oct. 93) JP–05,268,956, in *Chem Abst,* 120, 395, Abst. #72,415.
[001d]Sakai (31 Jul. 92) JP–04,210,593, in *chem Abst,* 117, Abst #229,115.
Knap et al. (1993) *J. Cardiovasc. Pharmarol.,* 22 (Suppl 8), S90–S93, in *Chem. Abst.,* 120(17), 549, Abst. #73,979.
Shinmi et al. (1993) *J. Cardiovasc. Pharmarol.,* 22 (Suppl 8), S61–S64, in *Chem. Abst.,* 120(17) 394–395, Abst. #211, 159.
Wilkinson et al. (1993) *Biochem. Soc. Trans.,* 21(3), 2765, Sigma Catalog (1990) p. 188, Cat #'s A9159 & A9910.
FEBS Letters, vol. 320, No. 2, pp. 165–168, Apr. 1993, Tatsuya Ohwaki, et al., "Endothelin–Converting Enzyme Activity in Human of Serun Lipoprotein Fraction".
Molecular Biology and Medicine, vol. 6, pp. 65–80, Jan. 23, 1989, James Scott, "The Molecular and Cell Biology of Apolipopritein–B".
Nature, vol. 323, No. 6090, pp. 734–738, Oct. 23, 1986, T. J. Knott, et al., "Complete Protein Sequence and Identification of Structural Domains of Human Apolipoprotein B".
Masashi Yanagisawa, et al., "A Novel Potent Vasoconstrictor Peptide Produced by Vascular Endothelial Cells", *Nature,* vol. 332, pp. 411–415 (1988).
Kenji Okada, et al., "Conversion of Big Endothelin–1 . . . ", Biochem. Biophys. Res. Commun., vol. 171, No. 3, pp. 1192–1198, 1990.
Tatsuya Sawamura, et al., "Purification and Characterization of Putative Endothelin . . . ", Biochem. Biophys. Res. Commun., vol. 168, No. 3, pp. 1230–1236, 1990.
Issei Komuro, et al, "Endothelin Stimulates c–fos and c–myc Expression . . . ", FEBS Letters, vol. 238, pp. 249–252, 1988.
Kazuo Kanno, et al., "Endothelin–1 and Vasculitis", JAMA, vol. 264, No. 22, p. 2868, 1990.
Amir Lerman, et al., "Circulating and Tissue Endothelin Immunoreactivity . . . ", N. Engl. J. Med., vol. 325, No. 14, pp. 997–1001, 1991.
Takeshi Horio, et al. "Increased Plasma Immonureactive Endothelin–1 . . . ", Atherosclerosis, vol. 89, pp. 239–246, 1991.
Terry J. Opgenorth, et al., "Endothelin–converting Enzymes", FASEB Journal, vol. 6, pp. 2653–2659, 1992.

*Primary Examiner*—David M. Naff
*Assistant Examiner*—Jon P. Weber
*Attorney, Agent, or Firm*—Oblon, Spivak, McClelland, Maier, & Neustadt

[57] ABSTRACT

A method for converting big endothelin-1 to endothelin-1 by contacting big endothelin-1 with a commercially available preparation of apolipoprotein B is presented. The apolipoprotein B itself has the converting enzyme activity.

1 Claim, 1 Drawing Sheet

METHOD OF CONVERTING BIG ENDOTHELIN-1 TO ENDOTHELIN-1 WITH HUMAN APOLIPOPROTEIN B

This application is a Continuation-in-Part Division of application Ser. No. 08/308,543, filed on Sep. 21, 1994, now abandoned.

BACKGROUND OF THE INVENTION

This invention relates to an endothelin converting enzyme consisting of apolipoprotein B and more particularly to the use of apolipoprotein B as an endothelin converting enzyme.

Endothelin is an endothelial cell-derived vascular smooth muscle constricting factor discovered by Yanagisawa et al. in 1988, the presence of which has been identified in porcine, bovine and human or the like [M. Yanagisawa et al., Nature, Vol. 332, 411 (1988)].

Endothelin includes three types of isopeptides which are named endothelin-1, endothelin-2 and endothelin-3, respectively. Of these isopeptides, endothelin-1 has been confirmed to show the highest activity in human body. Endothelin, having strong and lasting action of constricting vascular smooth muscle cell and trachea, induces hypertension and constriction of respiratory tract and also induces at a high concentration (about 1–50 pmol/ml in blood level) ischemic cerebral and cardiac diseases such as cerebral apoplexy, strenocardia, myocardial infarction, cardiac incompetence and arrhythmia, nephropathy such as nephritis, circulatory failure of lung, liver and intestine, and asthma, thus sometimes bringing animals to the death.

Endothelin-1 is a 21-amino acid peptide which is produced by cleaving its precursor peptide, big endothelin-1 of the formula (SEQ ID NO: 1:

```
Met—Leu—Ser—Ser—Cys—Ser—Cys   N
 |              /       \         ↓
Asp—Lys—Glu—Cys—Val—Tyr—Phe—Cys—His—Leu—Asp—Ile—Ile—Trp—Val—Asn
                                                                |
                                                               Thr
                                                                |
                                                               Pro
                                                                |
                                                               Glu
                                                                |
  C   Ser — Arg — Pro — Ser — Gly — Leu — Gly — Tyr — Pro — Val — Val — His
``` with the endothelin converting enzyme at the bond between the tryptophane residue at the 21st position from the N-terminus and the valine residue at the 22nd position from the N-terminus (shown by the downward arrow). This hydrolysis process is considered to be essential for production of endothelin-1 in vivo. Endothelin converting enzymes of bovine origin are those derived from cultured bovine endothelial cells or the like [K. Okada et al., Biochemical and Biophysical Research Communications, 171, No. 3, 1192 (1990)] and those derived from bovine adrenal medulla [T. Sawamura et al., Biochemical and Biophysical Research Communications, 168, No. 3, 1230 (1990)]. Regarding endothelin converting enzymes of human origin, WO 92/13944 discloses those prepared from human lung.

Endothelin having remarkable physiological activities as described above is produced enzymatically from its precursor i.e. big endothelin. Therefore, the elucidation of the endothelin converting enzyme will provide a means for inhibiting the production of endothelin in vivo. In addition, this endothelin converting enzyme is expected to provide a useful reagent for analyzing the mechanism of vasoconstriction in vivo and for studying various diseases induced by endothelin.

Further, the elucidation of the endothelin converting enzyme (ECE) will provide an effective tool for searching and developing an ECE-inhibitor which would be clinically useful in the prophylaxis and treatment of various diseases (hyperendothelinemia) induced by hypersecretion of endothelin, such as hypertension, constriction of trachea, ischemic brain diseases and heart diseases, nephropathy, circulation failure of various organs (e.g., liver, lung, intestine, etc.), and asthma or the like.

Many reports were made on the relationship between atherosclerosis and endothelin. Atherosclerosis is a pathologic condition progressing by the abnormal proliferation of vascular smooth muscle cells. Further, Komuro, I. et al by FEBS Lett., 238, 249–252 (1988) have reported that ET-1 functions as a strong growth factor of vascular smooth muscle cells. Kanno, K. et al by JAMA, 264, 2868 (1990) have reported that patients with atherosclerosis exhibit significantly increased plasma levels of ET-1 as compared with healthy humans. Lerman, A. et al by N. Engl. J. Med. 325, 997–1001 (1991) have reported that plasma ET-1 concentrations show positive correlation with the extent of atherosclerotic vascular lesions.

Regarding the correlation between hyperlipemia which is the most common risk factor for atherosclerosis and endothelin, Horio, T. et al by Atherosclerosis, 89 (1991), 239–246 have reported that plasma ET-1 concentration in hypercholesterolemic rats increases significantly as compared with normal rats and also that there is positive correlation between plasma total cholesterol levels and plasma ET-1 concentration in hypercholesterolemic rats. Furthermore, it has been reported that plasma ET-1 concentration has positive correlation with plasma VLDL (very low density lipoprotein) concentration and plasma LDL (low density lipoprotein) concentration, whereas it does not correlate with plasma HDL (high density lipoprotein) concentration.

From the above reports, it is considered that elevated plasma ET-1 level by hyperlipemia functions as a growth factor of vascular smooth muscle cells which contributes to the progress of atherosclerosis.

However, it remains unknown why plasma ET-1 concentration will increase by hyperlipemia.

SUMMARY OF THE INVENTION

As a result of intensive investigations to prepare endothelin converting enzyme from human origin being easily available, we have found that apolipoprotein B of human origin has an endothelin-converting enzyme activity.

Since apolipoprotein B itself is ECE and one of the elements constituting VLDL and LDL of which the plasma concentration is increasing in hyperlipemia, the mechanism on elevated plasma ET-1 concentration in hyperlipemia can be explained without contradiction. Thus, the present invention contributes largely to the explanation of such mechanism. By the invenstigation of inhibitors against the endothelin converting enzyme of the present invention i.e. apolipoprotein B, there can be provided a means for preventing an increase in plasma ET-1 concentration caused by hyperlipemia, eventually the development of atherosclerosis.

In an aspect of the present invention, there is provided an endothelin converting enzyme consisting of apolipoprotein B.

In another aspect of the invention, there is provided new use of apolipoprotein B as an endothelin converting enzyme.

In other aspects of the invention, there is provided a method of screening an inhibitor against the endothelin converting enzyme which comprises using the endothelin converting enzyme consisting of apolipoprotein B as a reference enzyme.

DETAILED DESCRIPTION OF THE INVENTION

Figure 1:
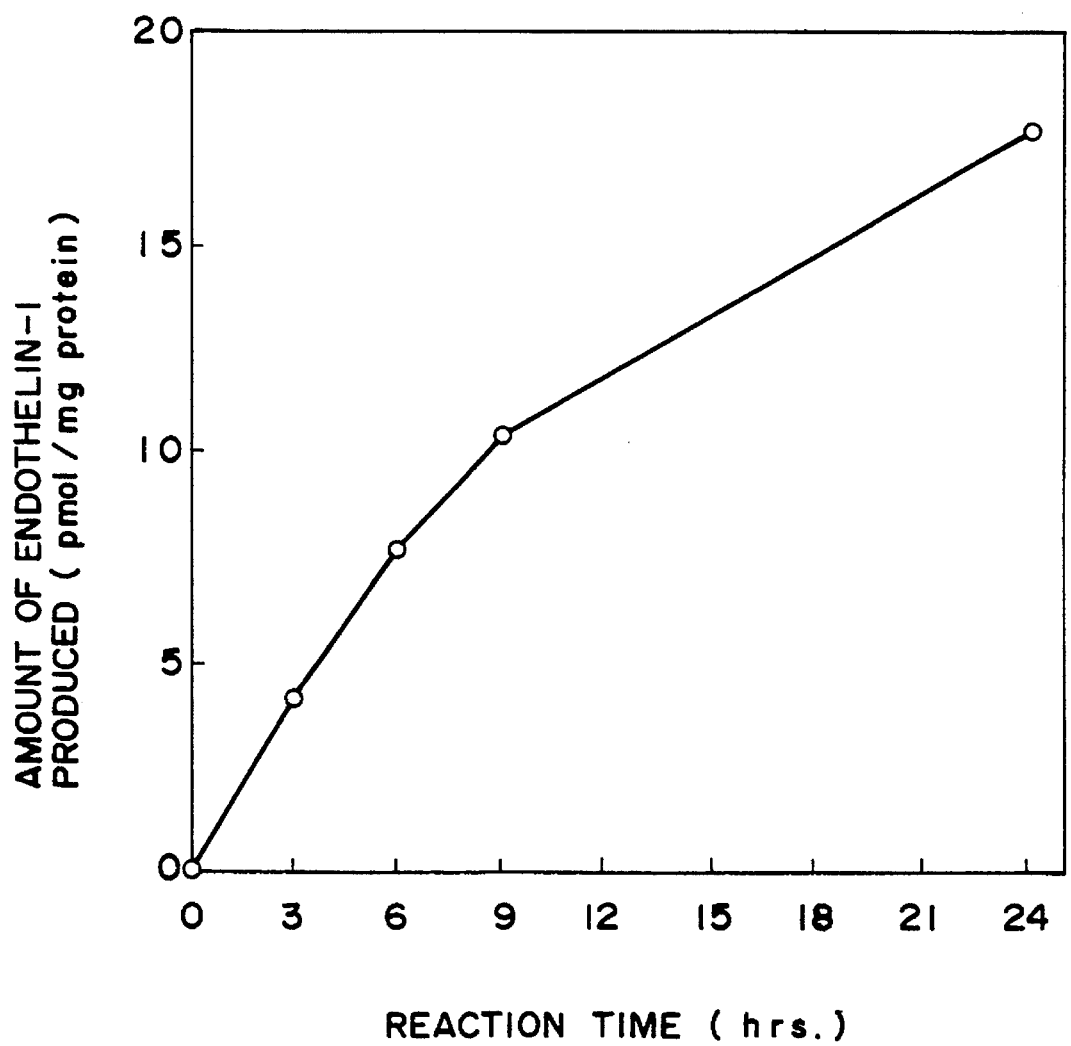
FIG. 1 is a graph showing a time course in the conversion of big endothelin-1 to endothelin-1 by apolipoprotein B obtained in Example 1.

The endothelin-converting enzyme activity of apolipoprotein B according to the invention is expressed in terms of the titer which is measured in the following manner.

(1) Measurement of ECE activity 0.15 mg of apolipoprotein B and 15 μl of a 20 nmol/ml big endothelin-1 solution was added to 0.3 ml of 10 mM Tris-HCl/0.15M NaCl buffer (pH 7.0), and the mixture was reacted at 37° C. for 6 hrs. After completion of the reaction, 6 μl of a 0.1M EDTA solution was added to cease the reaction.

Subsequently, the resultant endothelin-1 was assayed according to a sandwich enzyme immunoassay (EIA). An enzymatic activity of converting 1 pmol of big endothelin-1 to endothelin-1 per hour under the above-described reaction conditions is termed 1 U (unit).

(2) Sandwich-EIA method

A sample and an endothelin standard solution of a predetermined concentration were respectively applied to a 96-hole microplate on which anti-endothelin monoclonal antibody had been immobilized to thereby cause the reaction. After washing the microplate, peroxidase-labeled anti-endothelin polyclonal antibody was added to thereby cause the reaction. After washing the microplate, activity of bound peroxidase was assayed. Endothelin-1 in the sample was assayed based on the calibration curve drawn by using endothelin standard solutions having a predetermined concentration of endothelin.

When apolipoprotein B is used as a reference enzyme in screening of the inhibitors against endothelin converting enzymes, the inhibitory activity is measured by the following procedure. After incubating 0.15 mg of apolipoprotein B and various inhibitors in 0.3 ml of 10 mM Tris-HCl/0.15M NaCl buffer (pH 7.0) at 37° C. for 30 min., the remaining endothelin-converting enzyme activity was measured by the above-described method. Remaining activities in the presence of various inhibitors are compared with untreated activities to calculate the inhibitory activity of each inhibitor.

The invention is further illustrated by the following examples.

EXAMPLE 1

Conversion of big endothelin-1 to endothelin-1 by apolipoprotein B 0.5 mg of apolipoprotein B available from Sigma Chemical Co. (St. Lewis, Mo., USA) was dissolved in 1 ml of distilled water and the solution was dialyzed overnight against 10 mM Tris-HCL/0.15M NaCl buffer (pH 7.0) to prepare apolipoprotein B sample. To 0.3 ml of the apolipoprotein B sample was added 15 μl of human big endothelin-1 solution (20 nmol/ml) and the mixture was incubated at 37° C. for 0, 3, 6, 9 and 24 hrs. 6 μl of 0.1M EDTA solution was added to cease the reaction. The resultant endothelin-1 was determined by a sandwich enzyme immunoassay (EIA). The result is shown in FIG. 1. The activity of the present apolipoprotein B sample was found to be about 1.3 U/mg protein as calculated from the amount of endothelin produced 6 hrs. after the reaction.

To ascertain that apolipoprotein B itself has any ECE activity, the following experiment was performed.

To a solution of 0.25 mg of apolipoprotein B in 1 ml of 10 mM Tris-HCl/150 mM NaCl buffer (pH 7.0) was added 2.5 mg of anti-human apolipoprotein B IgG and the mixture was incubated at 4° C. for 24 hrs. To the incubated material was added 1 ml gel of protein G Sepharose (Pharmacia Co., Uppsala, Sweden) and the mixture was further incubated at 4° C. for 24 hrs. Apolipoprotein B was immunologically precipitated and the precipitate was centrifuged at 3000×g for 5 min. ECE activity in the resultant supernatant was measured. Remaining activity after immunoprecipitation is shown in Table 1 in terms of relative activity taking the activity of untreated enzyme (control) as 100.

TABLE 1

| Effect of Immunoprecipitation on ECE activity of apolipoprotein B | |
|---|---|
| | Relative Activity (%) |
| Control | 100 |
| After immunoprecipitation | 9 |

EXAMPLE 2

Evaluation for the inhibitory activity of inhibitor

To 0.3 ml of the apolipoprotein B sample obtained in Example 1 was added 3 μl solution of each inhibitor. After incubating the mixture at 37° C. for 30 min., 15 μl of human big-endothelin-1 solution (20 nmol/ml) was added. The mixture was further incubated at 37° C. for 6 hrs. The reaction was terminated by adding 6 μl of 0.1M EDTA solution. The resultant endothelin-1 was determined by sandwich enzyme immunoassay (EIA). Remaining activities in the presence of various inhibitors are shown in Table 2 in terms of relative activity taking the activity of untreated enzyme (control) as 100.

TABLE 2

| Inhibiror | Concentration (mM) | Relative Activity (%) |
|---|---|---|
| Control | — | 100 |

TABLE 2-continued

| Inhibiror | Concentration (mM) | Relative Activity (%) |
|---|---|---|
| Ethylenediaminetetraacetate (EDTA) | 1 | 1 |
| Phosphoramidon | 0.1 | 4 |
| Phenylmethanesulfonyl fluoride (PMSF) | 1 | 8 |
| Chymostatin | 0.01 | 25 |
| Thiorphan | 0.1 | 2 |

What is claimed is:

1. A method of converting big endothelin-1 to endothelin-1 comprising:

contacting said big endothelin-1 with isolated, purified human apolipoprotein B having a proteolytic activity for cleaving said big endothelin-1 to produce said endothelin-1.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 38 amino acids
      ( B ) TYPE: amino acid
      ( C ) STRANDEDNESS: single
      ( D ) TOPOLOGY: linear ( i x ) FEATURE:
      ( A ) NAME/KEY: Disulfide-bond
      ( B ) LOCATION: 1..15

( i x ) FEATURE:
      ( A ) NAME/KEY: Disulfide-bond
      ( B ) LOCATION: 3..11

( i x ) FEATURE:
      ( A ) NAME/KEY: Cleavage-site
      ( B ) LOCATION: 21..22

( x i ) SEQUENCE DESCRIPTION: SEQ ID NO:1:

```
Cys  Ser  Cys  Ser  Ser  Leu  Met  Asp  Lys  Glu  Cys  Val  Tyr  Phe  Cys  His
 1                  5                        10                       15

Leu  Asp  Ile  Ile  Trp  Val  Asn  Thr  Pro  Glu  His  Val  Val  Pro  Tyr  Gly
                20                       25                       30

Leu  Gly  Ser  Pro  Arg  Ser
               35
```